United States Patent
Müller et al.

(10) Patent No.: US 9,403,634 B2
(45) Date of Patent: Aug. 2, 2016

(54) ROTARY-SPINDLE SYRINGE

(71) Applicant: Ivoclar Vivadent AG, Schaan (LI)

(72) Inventors: Frank Müller, Feldkirch (AT); Lutz Vocke, Rorschach (CH)

(73) Assignee: Ivoclar Vivadent AG, Schaan (LI)

(*) Notice: Subject to any disclaimer, the term of this patent is extended or adjusted under 35 U.S.C. 154(b) by 0 days.

(21) Appl. No.: 14/265,569

(22) Filed: Apr. 30, 2014

(65) Prior Publication Data

US 2014/0332555 A1    Nov. 13, 2014

(30) Foreign Application Priority Data

May 7, 2013    (EP) .................................... 13166888
Jan. 10, 2014    (DE) ........................ 10 2014 100 266

(51) Int. Cl.
| | |
|---|---|
| B67D 7/60 | (2010.01) |
| G01F 11/00 | (2006.01) |
| B65D 83/00 | (2006.01) |
| B05C 17/005 | (2006.01) |
| A61C 5/06 | (2006.01) |
| A61M 5/24 | (2006.01) |
| A61M 5/28 | (2006.01) |
| A61M 5/31 | (2006.01) |

(52) U.S. Cl.
CPC ............ *B65D 83/0033* (2013.01); *A61C 5/062* (2013.01); *A61M 5/2425* (2013.01); *A61M 5/282* (2013.01); *A61M 5/3129* (2013.01); *B05C 17/00593* (2013.01)

(58) Field of Classification Search
CPC .......... B65D 83/0033; A61M 5/3158; A61M 5/31585; A61M 5/31586; A61M 5/3129; A61M 5/282; A61M 5/31528; A61M 5/3155; A61M 5/31551; A61M 5/31583; A61M 5/31581; A61M 5/2425; B05C 17/00593; A61C 5/062

USPC ............ 222/390, 41; 401/172, 173; 604/207, 604/211, 224
See application file for complete search history.

(56) References Cited

U.S. PATENT DOCUMENTS

| | | | | | |
|---|---|---|---|---|---|
| 1,252,719 | A | * | 1/1918 | Proctor | B43K 5/06 222/390 |
| 2,250,467 | A | * | 7/1941 | Cole | A61M 5/31591 604/211 |
| 2,626,087 | A | * | 1/1953 | Howard | B01L 3/0224 222/209 |
| 2,853,070 | A | * | 9/1958 | Julliard | A61M 5/20 604/224 |
| 2,874,877 | A | * | 2/1959 | Spencer | B41F 31/02 222/162 |
| 3,212,685 | A | * | 10/1965 | Swan | A61M 3/00 222/386 |
| 3,353,718 | A | * | 11/1967 | McLay | B01L 3/0224 222/158 |

(Continued)

FOREIGN PATENT DOCUMENTS

DE    19900792 C1    6/2000

*Primary Examiner* — J. Casimer Jacyna
*Assistant Examiner* — Benjamin R Shaw
(74) *Attorney, Agent, or Firm* — Ann M. Knab; Thad McMurray

(57) ABSTRACT

The invention relates to a rotary-spindle syringe, comprising a rotary element (24) with a thread which is in threaded engagement with the driver (40) wherein the driver (40) acts on a piston (16) and is mounted in a translationally moveable manner relative to the latter, and the rotary-spindle syringe (10) discharges material upon actuation of the rotary element (24) as well as upon application of pressure to a hand support (50) of the piston (16) or a plunger (62) of the piston (16).

15 Claims, 4 Drawing Sheets

(56) References Cited

U.S. PATENT DOCUMENTS

| | | | | |
|---|---|---|---|---|
| 3,572,556 A | * | 3/1971 | Pogacar | A61M 5/484 222/309 |
| 4,269,331 A | * | 5/1981 | Watson | A47G 19/183 222/390 |
| 4,583,974 A | * | 4/1986 | Kokernak | A61M 25/1018 604/211 |
| 5,290,260 A | * | 3/1994 | Stines | A61M 25/1018 222/390 |
| 5,336,183 A | * | 8/1994 | Greelis | A61M 25/1018 604/100.01 |
| 6,699,224 B2 | | 3/2004 | Kirchhofer et al. | |
| 8,974,465 B2 | * | 3/2015 | Schaeffer | B01F 15/0226 606/105 |
| 2002/0016571 A1 | * | 2/2002 | Kirchhofer | A61M 5/31553 604/218 |
| 2009/0302060 A1 | * | 12/2009 | Keller | B05C 17/0133 222/137 |
| 2010/0168677 A1 | * | 7/2010 | Gabriel | A61M 5/31551 604/189 |
| 2013/0043282 A1 | * | 2/2013 | Niklasson | A61M 5/31586 222/390 |

\* cited by examiner

ROTARY-SPINDLE SYRINGE

This application claims priority to German Patent Application No. 102014100266.0, filed Jan. 10, 2014 and European Patent Application No. 13166888.1, filed on May 7, 2013, all of which are hereby incorporated by reference.

The invention relates to a rotary-spindle syringe according to the preamble of claim 1.

A rotary-spindle syringe of this kind is, for instance, known from DE 199 00 792 C1 and corresponding U.S. Pat. No. 6,699,224 (B2), which is hereby incorporated by reference. In this rotary-spindle syringe it is possible to actuate a knurled wheel by turning it to discharge material. Furthermore, a translational movement can be realized by pulling back over the cover thereat.

However, this solution is unsuitable when it comes to rapidly discharging a substantial amount of material accommodated in the rotary-spindle syringe.

From DE 1 992 767 U1 and corresponding U.S. Pat. No. 3,572,556 (A), which is hereby incorporated by reference, a device for discharging fine doses is known which can discharge a liquid, namely upon actuation of a piston. The discharge of fine doses can be realized by adjusting a threaded cap which acts on a separate piston.

The production of this solution is relatively expensive and does not impart the typical shape to a syringe.

In contrast, the invention is based on the task of providing a compact and ergonomically simple-to-use rotary-spindle syringe according to the preamble of claim 1 which is suitable both for discharging fine doses and for discharging material rapidly.

This task is inventively solved by claim 1. Advantageous developments may be taken from the sub-claims.

To start with, the inventive solution features a compact syringe body comprising a housing, an outlet cannula and a plunger which can be operated intuitively. By applying pressure to the plunger which is either directly formed as a piston or acts on a piston material can be discharged from the outlet cannula rapidly and in an uncomplicated manner. In addition or as an alternative, by turning a rotary element which inventively acts on a driver and thus indirectly on the piston a discharge of fine doses can be realized. It is even possible to operate the syringe with one hand, i.e. in such a way that the user holds an outer sleeve, with respect to which the rotary element is turnable, between the three rear fingers of one hand and subsequently turns the rotary element via thumb and index finger relative to the outer sleeve.

According to the invention it is provided that the driver acts on the piston.

The driver moves laterally upon rotation of the rotary element, i.e. in the axial direction, relative to the cylinder which receives the material and, for instance, relative to the outer sleeve. Upon actuation of the plunger or piston for a rapid discharge of material a translational relative movement between driver and piston takes place. This ensures a dual use of the inventive rotary-spindle syringe to rapidly discharge material, on the one hand, and to discharge fine doses, on the other hand.

Upon actuation of the rotary element material can be discharged in fine doses according to the discretion of the user. Optionally, material can also be discharged upon the application of pressure to a hand support of the piston or a plunger of the piston.

According to the invention it is especially favorable that the entire movement path for the actuation of the driver for discharging the material is available by shifting the driver into the rearward area of the rotary-spindle syringe via the rotary element—when the syringe is completely filled. For this purpose, the rotary element comprises a correspondingly long internal thread which is in threaded engagement with a correspondingly shaped external thread of the driver.

The driver is disposed in a torque-proof manner relative to the outer sleeve and the cylinder and, upon turning the rotary element, it moves the piston to the front in order to discharge material in this way. Moving can be carried out either directly, such that the driver is in frictional contact with the piston, or indirectly, such that the driver acts on the piston and lies against it, for this purpose, in order to move it laterally.

In the first case, the piston can be pushed through by the driver by overcoming frictional contact in order to discharge material rapidly. In the second case, the piston is configured in a compact manner and can be actuated by a plunger which passes through the driver, without the need for frictional contact.

In a modified embodiment of the inventive rotary-spindle syringe it is provided to configure the rear part of the syringe body as a rotary element, or, if necessary, the entire outer surface of the syringe body. In the latter case, turning is carried out relative to the piston, which is guided in a torque-proof manner at the cylinder, in this case. Both cases are relatively easy to implement and possible at no expense; in the first case, cylinder and outer sleeve can be configured integrally which automatically results in a torque-proof connection.

According to the basic considerations of the present invention, cylinder, outer sleeve and driver are fixed to each other in a suitable manner wherein a torque-proof connection between piston and cylinder is not strictly necessary. The rotary element is mounted such that it is turnable relative to the remaining syringe body, but fixed in the axial direction such that a turning of the rotary element results in an axial movement of the driver.

According to the invention it is especially favorable that an intuitive operability of the inventive rotary-spindle syringe is ensured through the fluting on the outside of the rotary element, which can also be configured as a roughening or in any other suitable manner, together with the hand support at the plunger and a corresponding finger flange at the rear end of the outer sleeve.

Almost automatically, the user takes the finger flange of the rotary-spindle syringe with two fingers and then uses the thumb or ball of the thumb to push against the hand support for rapidly discharging material. On the other hand, he can take hold of the area of the rotary element either with the other hand or with the same hand and turn it. The turnability can be emphasized, if desired, by additionally disposing an arrow at the outer surface which indicates the direction of rotation.

According to the invention it is also favorable that the housing, i.e. the syringe body, can be colored in any suitable manner. For instance, the plunger or piston and the remaining syringe body can be colored in different colors to symbolize the corresponding material received in the rotary-spindle syringe. It is also possible to grant a visual insight into the expressed material via a transparent syringe body.

In a further advantageous embodiment an observation window is provided which shows the filling level of the material in the rotary-spindle syringe. Alternatively, at the piston or at any other suitable position a scale or other markings can be realized which shows the filling level of the rotary-spindle syringe.

Further advantages, details and features may be taken from the following description of two exemplary embodiments in conjunction with the drawings.

Figure 1:
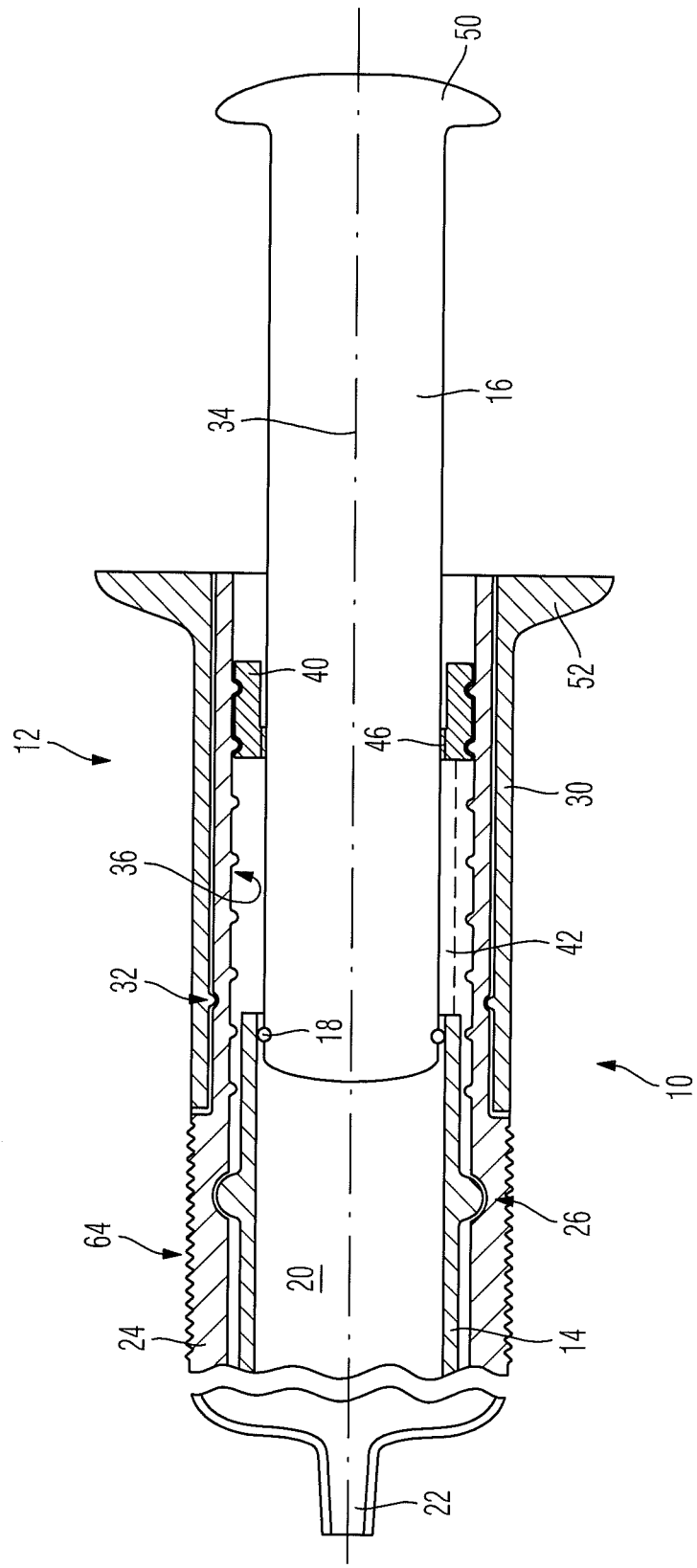
FIG. 1 shows a schematic section through an embodiment of an inventive rotary-spindle syringe.

The rotary-spindle syringe 10 illustrated in FIG. 1 comprises a syringe body 12 which is configured in several parts. A cylinder 14 receives a piston 16 in a translationally moveable manner known per se. A sealing ring 18, also known per se, ensures a sealing when the piston 16 is inserted into the cylinder 14. The cylinder 14 receives material 20 which can be discharged via an outlet cannula 22.

The cylinder 14 supports a rotary element 24 which is mounted in an axially fixed, yet rotatable manner to the cylinder 14. For this purpose, the cylinder 14 and the rotary element 24 comprise a plough-and-tongue joint 26. In the exemplary case, the plough groove is provided in the rotary element 24 and the tongue is provided at the cylinder 14, whereas it is to be understood that the design can also be interchanged.

An outer sleeve 30 is also mounted in a rotatable, yet axially fixed manner at the rotary element 24. For this purpose, a corresponding plough-and-tongue joint 32 is formed between the cylinder 14 and the outer sleeve 30 such that the outer sleeve 30 is indirectly mounted in an axially fixed manner to the cylinder 14.

An axis 34 runs through the piston 16 and also through the outlet cannula 22, and the inventive rotary-spindle syringe is formed in a centrosymmetrical manner relative to this axis 34.

According to the invention the rotary element 24 is provided with an internal thread 36. The internal thread 36 is in threaded engagement with a driver 40. It is mounted to the piston 16 such that it can be displaced axially. Via an angle arrangement which is constructed as a sword-shaped cylinder extension 42 in the exemplary embodiment illustrated it is supported in a torque-proof manner against the cylinder 14. This torque support prevents the driver 40 from being turned relative to the cylinder 14.

When turning the rotary element 24 relative to the remaining syringe body 12 the driver 40 is not turned as a result of this but moved in the axial direction due to the threaded engagement.

The driver 40 is mounted to the piston 16 by means of a support area 46. It is in frictional contact with the piston. Upon actuation of the rotary element 24 the piston 16 is thus moved in the direction of the outlet cannula 22 together with the driver 40 maintaining the frictional contact such that material 20 leaves the outlet cannula.

If material is to be discharged rapidly, a hand support 50 of the piston is actuated, namely against a finger flange 52 of the outer sleeve 30. Hereby, the piston 16 slides along the driver 40 in the support area 46 or slides through it, and material 20 is also discharged, namely relatively rapidly.

Figure 2:
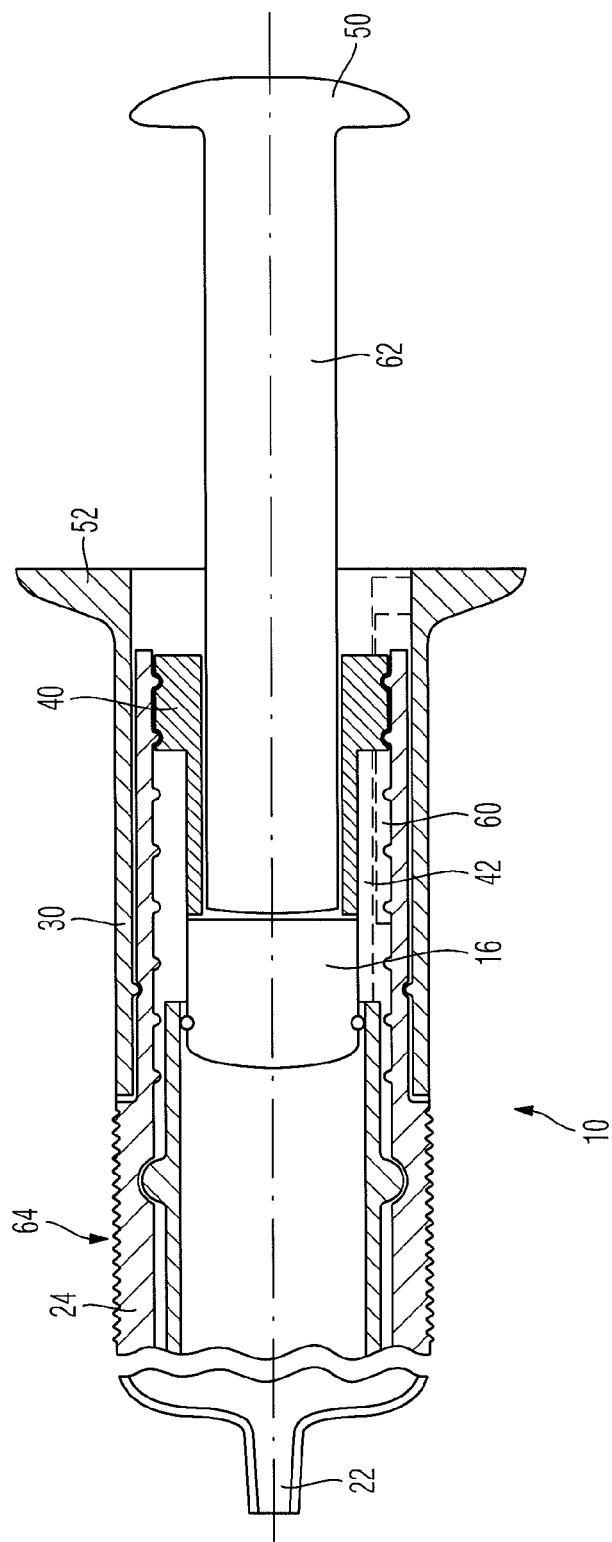
FIG. 2 shows a schematic section through a further embodiment of an inventive rotary-spindle syringe.

In order to ensure rotational support between the rotary element 24 and the remaining syringe body 12 also at the outer sleeve 30, the outer sleeve is preferably also connected to the cylinder 14 and thus to the driver 40 in a torque-proof manner. For this purpose, one possible implementation is illustrated in FIG. 2 via the rotation stop 60. The rotation stop 60 is supported against the sword-shaped cylinder extension 42 and thus forms a torque-proof connection, although the driver 40 has some play at the sword-shaped cylinder extension 42.

FIG. 2 further shows a modified design of the driver 40 and the piston 16. The driver 40 acts on the piston 16 in the axial direction which is constructed similar to a flat cylinder, at its outer circumference. It applies pressure in the direction of discharge, i.e. in the direction of the cannula 22, when the rotary element 24 is turned and thus the driver 40 is displaced axially.

In this embodiment, too, the driver 40 is provided with a passageway which extends through a plunger 62 which is in contact with the piston 16 and can advance the latter if material is to be discharged rapidly.

The design illustrated in FIG. 2 also offers the special advantage that the fast and finely-dosed discharge of material can be undertaken independently of one another. Precision manufacturing for the provision of an exact frictional force is not necessary.

In contrast, the embodiment according to FIG. 1 offers the special advantage that the rotary element does not have to be turned additionally if material has been discharged rapidly via the piston 16.

FIG. 1 and FIG. 2 further show the outer surface of the rotary element which is profiled or roughened 64 and extends in extension to the remaining syringe housing body and is flush with the syringe housing body with minimal or no gap between the syringe body and the rotary element.

Figure 3:
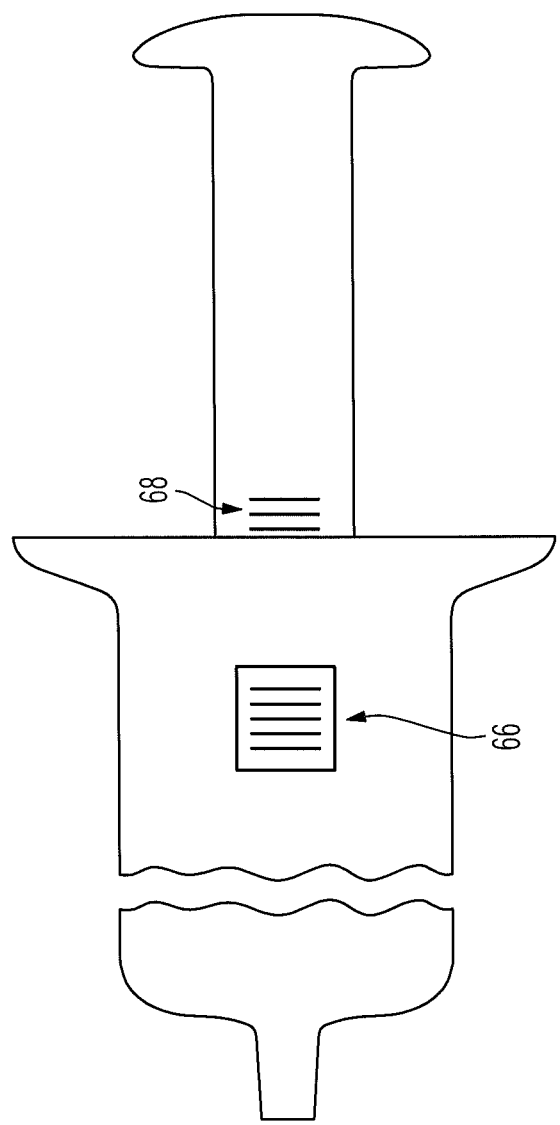
FIG. 3 shows an embodiment of the inventive rotary-spindle syringe displaying the level indicator and the window.

FIG. 3 shows the rotary-spindle syringe with a level indicator 68 attached to the piston 16 by a marking or a scale at the piston 16 which is visible through a window 66 in the outer sleeve. Alternatively, level indicator 68 could also be attached to outer sleeve 30.

Figure 4:
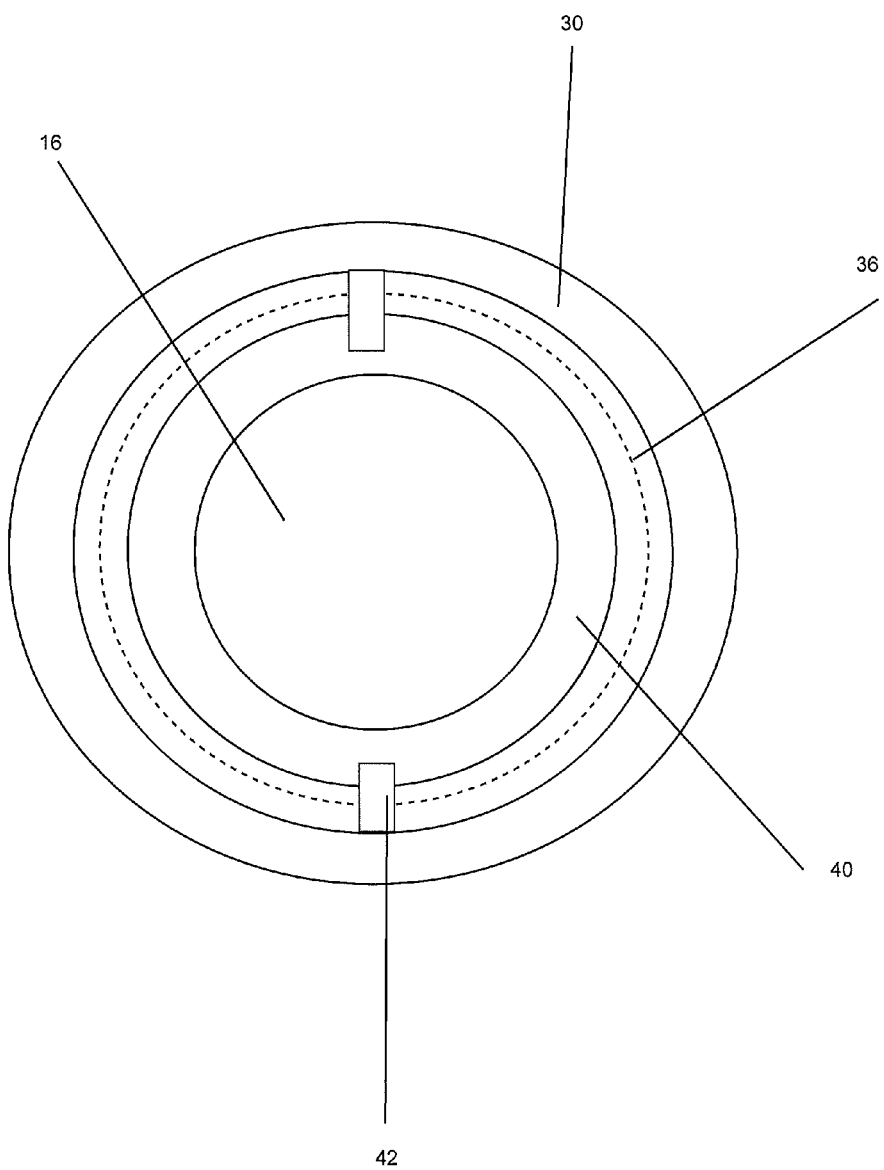
FIG. 4 shows a schematic section of an embodiment of the inventive rotary spindle syringe showing the sword-shaped cylinder extension.

FIG. 4 shows a sectional view of rotary-spindle syringe 10 with the sword-shaped cylinder extensions 42 in a torque-proof manner that prevents the driver 40 from being turned relative to the cylinder 14.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A rotary-spindle syringe, comprising
a rotary element with a thread which is in threaded engagement with a driver,
wherein the driver acts on a piston and is mounted in a translationally moveable manner relative to the piston,
wherein the driver is completely covered by an outer sleeve, and
wherein the rotary-spindle syringe discharges material upon application of pressure to a hand support of the piston or a plunger of the piston.

2. The rotary-spindle syringe according to claim 1, wherein the rotary element is disposed adjacent to the outer sleeve of the rotary-spindle syringe and is rotatable relative to a remaining syringe body.

3. The rotary-spindle syringe according to claim 1, wherein the outer surface of the rotary element which is profiled or roughened extends in extension to a remaining syringe body and is flush with the syringe body with minimal or no gap between the syringe body and the rotary element.

4. The rotary-spindle syringe according to claim 1, wherein the rotary element moves the piston via the driver for discharging the material from the rotary-spindle syringe.

5. The rotary-spindle syringe according to claim 1, wherein the driver acts on the piston through contact by friction, wherein piston can be moved towards the outlet end of the rotary-spindle syringe either upon actuation of the plunger or of the driver.

6. The rotary-spindle syringe according to claim 1, wherein the driver is held in a torque-proof manner at an inner cylinder along which the piston is guided, via an anti-rotation stop, and is in threaded engagement with the rotary element.

7. The rotary-spindle syringe according to claim 1, wherein the driver is connected with the piston through frictional contact and carries it along upon turning the rotary element in the outlet direction.

8. The rotary-spindle syringe according to claim 6, wherein the anti-rotation stop comprises a sword-shaped cylinder extension and the driver is disposed in frictional contact with the piston and is guided along the sword-shaped cylinder extension in a torque-proof manner.

9. The rotary-spindle syringe according to claim 1, wherein the piston is mounted slidably relative to the driver by overcoming frictional contact.

10. The rotary-spindle syringe according to claim 1, wherein an inner cylinder is mounted slidably to the driver element in an axially fixed fashion, and is snap fitted into that position.

11. The rotary-spindle syringe according to claim 1, wherein a level indicator is attached to the piston and/or the outer sleeve by means of a marking or a scale at the piston which is visible through a window in the outer sleeve.

12. The rotary-spindle syringe according to claim 1, wherein the driver is in the rear part of the rotary-spindle syringe when the rotary-spindle syringe is filled with material, and is drawn to the front, towards an outlet cannula, by the rotary element upon actuation of the rotary element.

13. The rotary-spindle syringe according to claim 1, wherein upon actuation of the rotary element the driver applies pressure to a piston for discharging material through an outlet cannula, and wherein the plunger is guided in or at the driver and also applies pressure to the piston when material is discharged from the outlet cannula by actuating the plunger.

14. The rotary-spindle syringe according to claim 2, wherein the rotary element is rotatable relative to the outer sleeve of the syringe body.

15. The rotary-spindle syringe according to claim 6, wherein the anti-rotation stop comprises a sword-shaped cylinder extension.

* * * * *